United States Patent
Desjardins et al.

(10) Patent No.: US 12,096,766 B2
(45) Date of Patent: Sep. 24, 2024

(54) PROCESS FOR COOLING A BIOLOGICAL MATERIAL AND THE STORAGE THEREOF

(71) Applicant: GENIALIS, Henrichemont (FR)

(72) Inventors: Isabelle Desjardins, Henrichemont (FR); Guillaume Gillet, Salbris (FR)

(73) Assignee: Genialis, Henrichemont (FR)

( * ) Notice: Subject to any disclaimer, the term of this patent is extended or adjusted under 35 U.S.C. 154(b) by 830 days.

(21) Appl. No.: 16/481,957

(22) PCT Filed: Jan. 30, 2018

(86) PCT No.: PCT/FR2018/050208
§ 371 (c)(1),
(2) Date: Jul. 30, 2019

(87) PCT Pub. No.: WO2018/138461
PCT Pub. Date: Aug. 2, 2018

(65) Prior Publication Data
US 2019/0343114 A1    Nov. 14, 2019

(30) Foreign Application Priority Data
Jan. 30, 2017 (FR) .................... 17 50745

(51) Int. Cl.
*A01N 1/02* (2006.01)
(52) U.S. Cl.
CPC ......... *A01N 1/0284* (2013.01); *A01N 1/0257* (2013.01); *A01N 1/0289* (2013.01)
(58) Field of Classification Search
CPC ... A01N 1/0284; A01N 1/0257; A01N 1/0289
USPC .......................................... 435/1.3
See application file for complete search history.

(56) References Cited

U.S. PATENT DOCUMENTS

| | | | |
|---|---|---|---|
| 4,559,298 A * | 12/1985 | Fahy | A01N 1/0289 62/78 |
| 4,688,387 A | 8/1987 | Conaway | |
| 6,381,967 B1 * | 5/2002 | Craig | A01N 1/0257 34/284 |
| 9,417,166 B2 | 8/2016 | Thorne et al. | |

(Continued)

FOREIGN PATENT DOCUMENTS

| | | | |
|---|---|---|---|
| DE | 102011115467 A1 | 4/2013 | |
| EP | 0232672 A1 | 8/1987 | |
| KR | 101129331 B1 * | 3/2012 | |

(Continued)

OTHER PUBLICATIONS

Lebrun, An Introduction to Cryogenics, 2007, European Organization for Nuclear Research Laboratory for Particle Physics (Year: 2007).*

(Continued)

*Primary Examiner* — Michael L Hobbs
*Assistant Examiner* — Lenora A Abel
(74) *Attorney, Agent, or Firm* — Bachman & LaPointe, P.C.

(57) ABSTRACT

A high pressure cryogenic process for cooling a biological material, comprising the solidification of the biological material by a cryogenic fluid, wherein the solidification of the biological material is carried out at a cryogenic temperature at a pressure of at least 10 bar and the cryogenic fluid is present in an amount greater than 200 kg/m3.

9 Claims, 3 Drawing Sheets

(56) References Cited

U.S. PATENT DOCUMENTS

2009/0011505 A1    1/2009  Leunissen
2014/0260346 A1    9/2014  Fuhr et al.

FOREIGN PATENT DOCUMENTS

WO    WO-9966271 A1 * 12/1999   ............... A01N 1/02
WO       2007123720 A2   11/2007

OTHER PUBLICATIONS

European Organization for Nuclear Research Laboratory for Particle Physics (Year: 2007).*
Machine English Translation KR101129331B1 (Year: 2012).*
Le Bui, Tony Vien, Cryopreservation, culture recovery and glucose induced programmed cell death in chlorophyte microalgae, Thesis, The University of Queensland, 2014, pp. 1-111.
Pribenszky, C et al., "Improving post-thaw survival of cryopreserved mouse blastocysts by hydrostatic pressure challenge", Animal Reproduction Science, Elsevier Science Publishers, Amsterdam, NL, vol. 87. No. 1-2, Jun. 1, 2005, pp. 143-150, XP027622634, ISSN: 0378-4320.
ISR dated May 14, 2018 for PCT/FR2018/050208.
Numerical study of flow and heat-transfer characteristics of cryogenic slush fluid in a horizontal circular pipe (SLUSH-3D), Katsuhide Ohira et al., Cryogenics 52 (2012) pp. 428-440 (cited in European counterpart application on Feb. 2, 2023).

* cited by examiner

PROCESS FOR COOLING A BIOLOGICAL MATERIAL AND THE STORAGE THEREOF

BACKGROUND

The present invention relates to the treatment of biological materials in order to preserve same over time. In particular, it relates to the preservation of biological materials by pressurized cryogenics.

STATE OF THE ART

The principle of cryogenics consists in exposing a biological material to cold. The first tests began in the 1950s with the preservation of human and bovine semen which is biological material in suspension. A temperature is said cryogenic when it is below 93.15K according to a definition of the US National Institute of Standards and Technology. However, by extension, applications using the immersion in liquid gas up to 170K, or using spraying such gases up to 230K, IQF cryogenic tunnels (Individually Quick Frozen) for example, are considered to be cryogenic applications. The idea is that at a low temperature of about 190K, the chemical activities normally occurring within the biological material stop and below 140K, all non-crystalline bodies are glassy and thus completely stabilized. Thus, the metabolism, ageing and death processes do not occur, which makes it possible for the biological material to remain intact in a frozen state.

Cryogenics has then been adapted to the preservation of other biological materials such as human blood components (e.g. erythrocytes).

In the 1960s, organ transplantation surgical procedures were developed. However, practitioners face three major problems: the rejection by the patient of the transplanted organ, the availability of a compatible organ with the patient and the limited life of the organ outside the body.

Therefore, cryogenic preservation has, for many years, given practitioners, but especially the patients waiting for a transplant hopes, because it made it possible to preserve, in the long-term, organs which had, most of the time, been removed upon the donor's death and thus having an organ bank would solve the three problems mentioned above.

Cryogenic processes for preservation are difficult to use not because of the viability of the biological material in extreme cryogenic temperatures conditions, but because of the existence of an intermediate temperature range between the room temperature and the lethal cryogenic temperature therefor. This temperature range is between about 220K and about 255K. The biological material is not exposed to this range of temperatures once, but twice: a first time during the lowering of the temperature to a cryogenic temperature for its preservation and a second time during the warming to room temperature for use.

At this temperature, the water contained in the biological material is transformed into ice and its volume increases (by about 10%): the ice crystals formed outside the cells are large in size and their shape causes the perforation of the cell membranes.

If cooling is slow, the water outside the cell tends to turn into ice, which causes water osmosis, and moves it from the inside of the cells to the outside thereof. When water escapes from the cells, the concentration of the solutes inside these dangerously increases to the point of becoming lethal.

In order to avoid the formation of ice, some cryogenic preservation methods use active cryoprotectants, typically glycerol, dimethylsulfoxide, glycol alkenes or other compounds capable of strongly binding with water by hydrogen bonding. This capability prevents water from freezing by lowering the solidification temperature. The higher the amount of active cryoprotectants, the lower the solidification temperature.

However, the active cryoprotectants are generally effective only for the preservation of the biological material in suspension in the form of individually dissociated cells.

Moreover, using active cryoprotectants is not safe for the biological material. As a matter of fact, in high concentration, the active cryoprotectant itself becomes harmful to the biological material and contributes to the death of the latter.

In addition, there is the problem of removing the active cryoprotectant prior to using the biological material.

Eventually, even in the presence of active cryoprotectants, the biological material cells surviving cryogenic preservation are few.

Other methods involve pressure to lower the water-to-ice transformation temperature. For example, Tony Vien Bui's thesis (Cryopreservation, cultural recovery and glucose induced programmed cell death in chlorophyte microalgae, The University of Queensland, 2014 address the issue of pressurized cryogenics using equipment especially designed for electron microscopy. These works mention a survival rate not exceeding 1%.

Thus, the need for a process for the preservation of biological materials with a high survival rate is still felt.

SUMMARY

An objective of the present invention is to overcome at least one of the disadvantages of the prior art described above and in particular to allow the preservation of biological materials with a high survival rate and in particular without using active cryoprotectants.

For this purpose, the present invention provides for a cryogenic process for cooling a biological material under pressure, comprising solidification of the biological material by a cryogenic fluid, characterized in that the solidification of the biological material is carried out at a cryogenic temperature, at a pressure of at least 10 bars and the cryogenic fluid is present in a quantity greater than 200 kg/m3.

The joint setting of the cryogenic temperature, pressure and the quantity of cryogenic fluid enables to significantly improve the cell survival rate of the biological material to be preserved. Indeed, the present inventors have surprisingly found that the temperature and pressure are not the only parameters to ensure good survival rates, taking into account the quantity of cryogenic fluid is also important.

Other optional and non-limiting characteristics are as follows.

The introduction of the biological material into a chamber containing a cryogenic fluid; and the setting of the desired conditions of temperature, pressure and quantity of cryogenic fluid within the chamber to a cryogenic temperature, so that the pressure inside the chamber is at least 10 bars and the quantity of cryogenic fluid in the chamber is greater than 200 kg/m.

The temperature is preferably controlled to be less than 170K.

The pressure is preferably adjusted to be greater than 20 bar.

The quantity of cryogenic fluid in the chamber is preferably adjusted to be greater than 250 kg/m3.

The biological material may be previously contained in suspension in a liquid mixture; the setting of the desired conditions made before the introduction of the biological material into the chamber; and the introduction of the biological material produced by injection of the liquid mixture into the chamber.

The chamber may comprise a first chamber portion and a second chamber portion, the internal volumes of the first and second chamber portions being separate at the beginning; the step of introducing comprising the provision of biological material in the first chamber portion free of cryogenic fluid, the provision of the cryogenic fluid disposed in the second chamber portion and the joining of the first chamber portion with the second chamber portion to form the chamber so that their internal volumes are linked; setting the desired conditions being provided in the second chamber portion so as to achieve the desired conditions within the chamber after the joining of the first chamber portion with the second chamber portion.

The cryogenic fluid may be in liquid or supercritical form.

The invention also provides a biological material preservation cryogenic process under high pressure, comprising the steps of the process described above, the depressurization of the chamber to the atmospheric pressure and the provision of biological material solidified in a freezer.

The present invention also provides for a frozen product comprising pre-treated frozen biological material and having a survival rate after thawing of the biological material of at least 45%.

BRIEF DESCRIPTION OF THE DRAWINGS

Other objects, features and advantages will become apparent from reading the following description with reference to drawings, including.

The following description and the drawings are given for illustrative and not limiting purposes.

DETAILED DESCRIPTION

Figure 1:
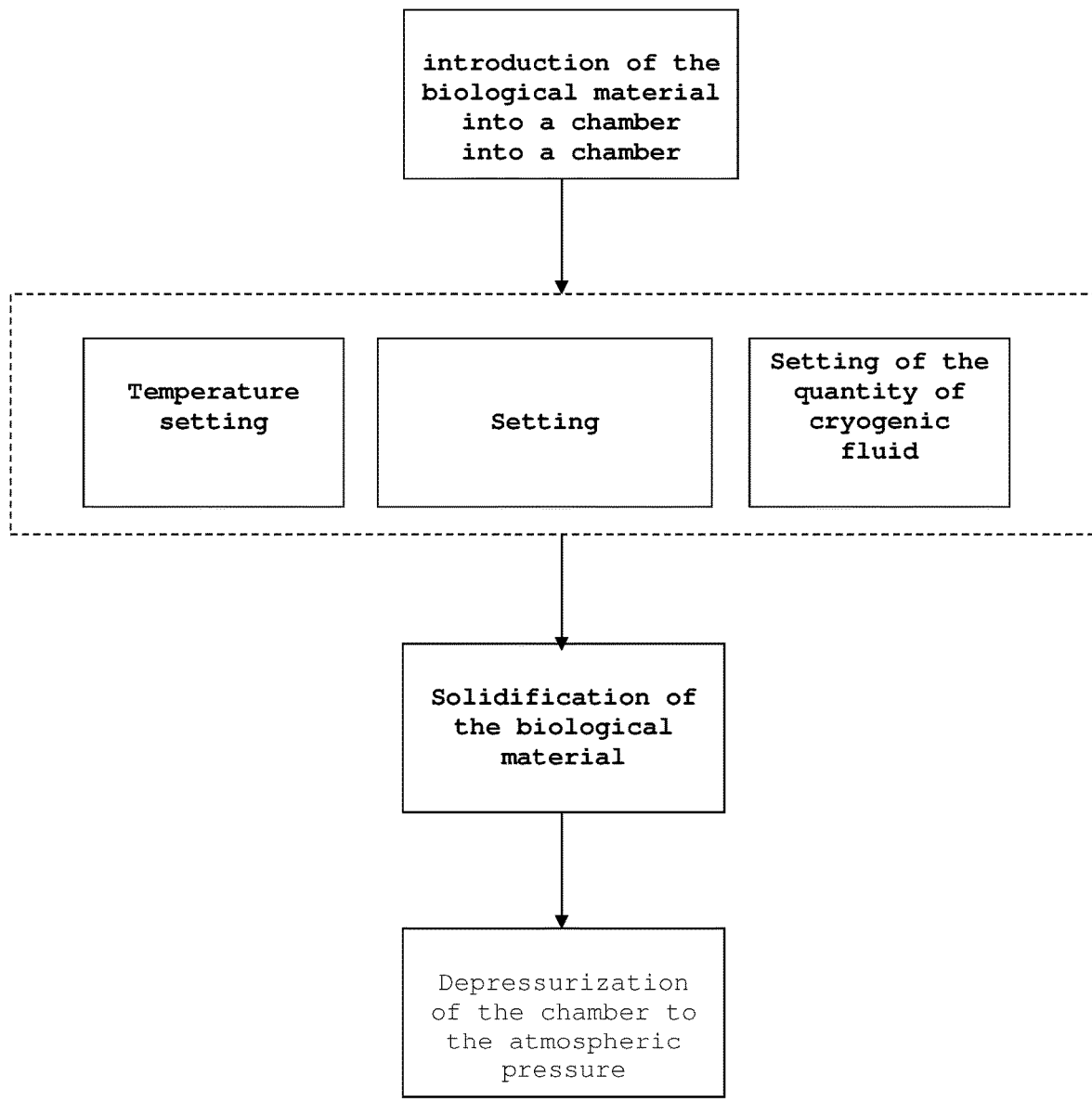
FIG. 1 is a flowchart showing the steps of the method for cooling a biological material according to an example of the invention.
Figure 2:
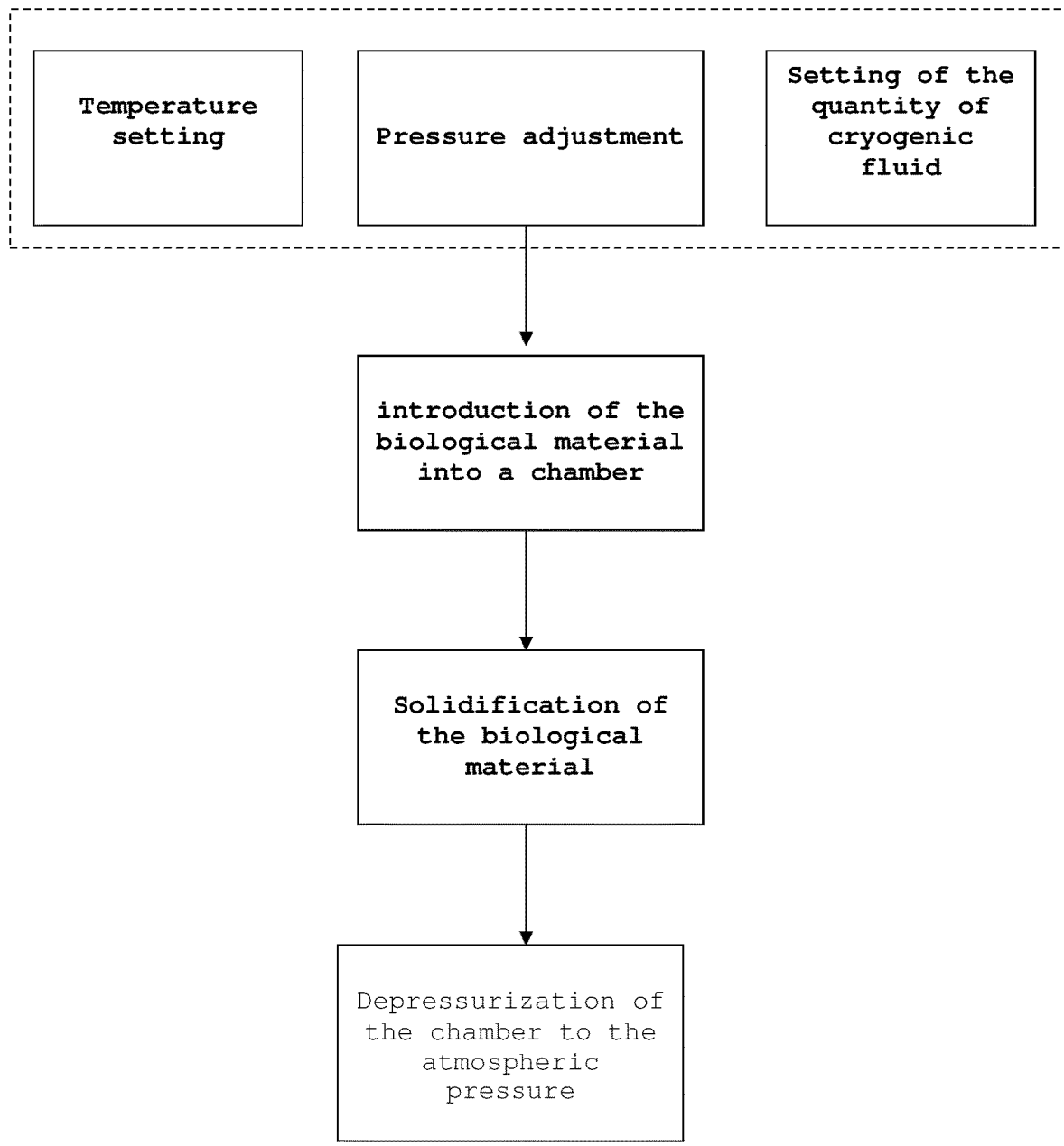
FIG. 2 is a flowchart showing the steps of the method for cooling a biological material according to another example of the invention.
Figure 3:
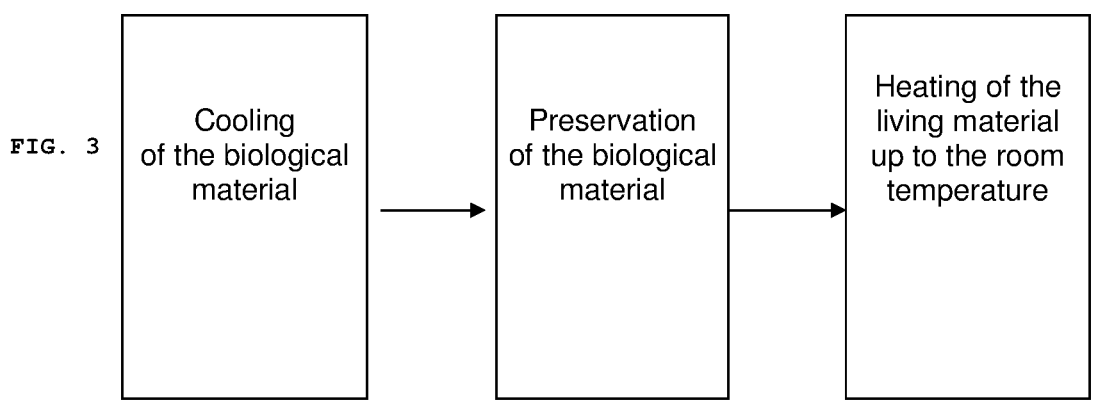
FIG. 3 is a flow chart showing the steps of a method for preserving and thawing biological material according to another example of the invention.

A cryogenic process for cooling biological material according to the present invention will be described below with reference to FIGS. 1 to 3.

This process is carried out under pressure and comprises the solidification of the biological material by a cryogenic fluid. Solidifying the organic material takes place at a cryogenic temperature at a pressure of at least 10 bars and the cryogenic fluid is present in a quantity greater than 200 kg/m.

Preferably, the process further comprises before the solidification step:
the introduction of the biological material into a chamber containing a cryogenic fluid; and
the setting of the desired condition of temperature, pressure and quantity of cryogenic fluid within the chamber to a cryogenic temperature, so that the pressure inside the chamber is at least 10 bars and the quantity of cryogenic fluid in the chamber is greater than 200 kg/m.

The terms "biological material" must be understood throughout this paper as any material composed of at least one cell and any other naturally occurring element in a biological organism. The identity of the biological organism does not matter and depends on the intended use of the preserved biological material. In particular, the biological organism can be human or non-human. The cell included in this material is preferably alive, that is to say that the majority of chemical processes that occur naturally in the cell still occur. Examples of biological material are: a unicellular microorganism, a multicellular microorganism, a cell of a multicellular organism, or part of a tissue or the whole or part of an organ. Among the unicellular microorganisms, yeast (e.g., *Saccharomyces* such as *S. cerevisiae* and *S. boulardii*), bacteria (eg *Lactobacilli* such as *L. delbrueckii*, including *L. bulgaricus* and *Streptococcus* such as *S. thermophilus*) and some algae (e.g. diatoms) can be mentioned. The cells of a multicellular organism include stem cells, gametes, some algae (e.g. *Arthrospira platensis* such as A. and *A. maxima* commonly known as *spirulina* and used as a food supplement) and filamentous fungi (e.g.: *Penicilliums* such as *P. roqueforti* and *P. camemberti*). Among the organs the heart muscle, kidneys, pancreas, liver, a limb (arm, hand, leg, foot), a joint (elbow, knee) and one eye can be mentioned. The tissues include bone marrow and skin. Preferred examples of biological material are: (pathogen and non-pathogen) microorganisms, stem cells and organs.

The terms "cryogenic fluid" means, in this paper, and contrary to the definition of the US National Institute of Standards and Technology, a liquid, a gas or a compound in a supercritical state, which in the state in question has a temperature below 170K, preferably below 150K. in general, cryogenic fluids exhibit a very low boiling point, typically below 120K at the atmospheric pressure. Examples of cryogenic fluids (the boiling point is specified in parentheses): Helium (5.19K for helium 3; 4.214K helium 4), hydrogen (20.27K), neon (27.09K), nitrogen (77.36K), air (78.8K), argon (87.24K), oxygen (90.19K). The preferred cryogenic fluid is nitrogen for its ease of access and use. The cryogenic fluid, whatever its nature, is preferably used in liquid or supercritical form. Thus, conditions of temperature, pressure and quantity are preferably selected so that the cryogenic fluid is present inside the chamber only in the liquid or only in the supercritical state.

The introduction of the biological material into the chamber comprising the cryogenic fluid creates a contact thereof with the latter. The introduction may be in particular carried out by dipping the biological material directly into the cryogenic fluid.

The setting of temperature, pressure and the quantity of cryogenic fluid should be understood as an adjustment making it possible to obtain the desired conditions within the chamber comprising the cryogenic fluid and the biological material during the cooling thereof. Thus, the temperature, pressure and the quantity of cryogenic fluid, prior to the introduction of the biological material into the chamber, can differ from the temperature, pressure and quantity of cryogenic fluid for the desired cold solidification of the biological material.

The desired conditions setting step can occur before, during or after the introduction of the biological material into the chamber.

The temperature is preferably controlled to be less than 170K, 150K, 140K, 120K, 100K, 80K. Preferably, the temperature is set to be above 4K, more preferably above 30K, even more preferably above 70K.

Pressure is preferably set so as to be greater than 20 bars, 30 bars, 40 bars, 50 bars, 60 bars, 70 bars, 80 bars, 90 bars, or 100 bars. Preferably, the pressure is set between 10 and 1000 bars, 10 and 500 bars, 10 and 250 bars, 10 and 100 bars. For example, the pressure may be 10, 20, 30, 40, 50, 60, 70, 80, 90, 100, 150, 200, 250, 300, 350, 400, 450, 500, 725, 1000 bars.

The quantity of cryogenic fluid contained in the chamber is set to be above 200 kg/m3, preferably above 250 kg/m3, more preferably above 300 kg/m3, yet preferably above 350 kg/m3, still preferably above 400 kg/m3. Preferably, the quantity of cryogenic fluid is set to be less than 850 kg/m3, 825 kg/m3, 800 kg/m3.

The upper and lower limits mentioned above for the temperature, pressure and quantity of fluid can be freely combined as needed.

The method advantageously further comprises a depressurization step of the chamber to the atmospheric pressure. It is preferably carried out in a controlled manner for obvious security reasons; too abrupt a release might lead to a displacement of the chamber and the endangerment of the persons present.

In a first embodiment, the biological material is contained in suspension in a liquid mixture. The liquid mixture wherein the biological material is suspended may for example be selected from: a culture medium, a salt solution, water or a food product (fruit or vegetable juice for example). Preferably, the liquid mixture includes very little, or even no active cryoprotectants. That is to say, it comprises less than 1% by weight of active cryoprotectants, preferably less than 0.1, more preferably less than 0.01, still preferably 0%.

In this case, the desired conditions are preferably set before the biological material is introduced into the chamber. Still in this case, the biological material is preferably introduced by injection of the liquid mixture into the chamber.

The cryogenic fluid is preferably in liquid or supercritical form. Using the cryogenic fluid in supercritical form is particularly advantageous for the biological material (individual cells) suspended in a liquid mixture.

This first embodiment generally results in forming solid lumps of mixture comprising the biological material. These solid lumps are generally in the form of spherical or ovoid beads or granules. The geometry of the solid lumps generally depends on the viscosity of the liquid mixture containing the biological material in suspension, the size and shape of the injection nozzles used, and the injection rate.

For example, a viscosity of product equal to 2 cP passing through nozzles, 3 mm in diameter and 40 mm long at a rate of 8 mL/min will form spherical balls, whereas a viscosity of the product equal to 13,000 cP passing through the same nozzle at a rate of 200 mL/min will form cylindrical granules. Viscosity is measured using a falling ball viscometer.

The injection may be carried out using a piston pump or any other suitable mechanism. The piston pump may comprise one or more nozzle(s).

In a second embodiment, the chamber comprises a first chamber portion and a second chamber portion, the internal volumes of the first and second chamber portions being separated at the beginning. In other words, the chamber is formed of two portions to be brought into fluid communication for the solidification of the biological material. A two-portion chamber may for example include a cylindrical, preferably round bottomed, vessel adapted to the pressure and temperature conditions of the inventive method, the inside of which consists of a double-shell system. Each cylindrical shell is thus adapted to the processing conditions of the inventive method and the two volumes can be joined via the opening of a valve or the release of a check-valve, artfully placed at the interface thereof. An equivalent system can be achieved through two chambers connected by a circuit containing a valve, the opening of which makes it possible to join the two volumes when it is opened.

In this case, the introducing step may include the provision of the biological material in the first chamber portion free of cryogenic fluid, the provision of the cryogenic fluid in the second chamber portion and the joining of the first chamber portion with the second chamber portion to form the chamber so that their internal volumes are in fluid communication. Still in this case, the desired condition setting step may be performed in the second chamber portion so as to achieve the desired conditions within the chamber after connecting the first chamber portion with the second chamber portion.

The joining of the two chamber portions is typically performed quickly and brutally, within a few seconds.

The second embodiment is particularly advantageous for the biological material in solid form at the beginning of the process. For example, the biological material is all or part of an organ or a tissue.

The cooling method described above is advantageously part of a process for preserving the biological material. Such a process for preserving the biological material then comprises the steps of the cooling method described above and further the transfer of the solidified biological material into a freezer at a temperature below 0° C., preferably below −10° C., more preferably below −15° C. and preferably above −80° C., −60° C. and more preferably above −40° C. The solidified biological material is in particular extracted from the chamber before being transferred to a freezer.

The frozen product obtainable by the above process comprises the (human or non-human) frozen pretreated biological material and having a survival rate after thawing of the biological material of at least 45%, preferably at least 50%, 60%, 70%, 80%, 90%, 95%, 98%.

The present invention also provides a product recovery method that can be obtained by the cooling method described above. This thawing method comprises the steps of introducing the solidified biological material into a chamber brought to the product preservation temperature, the increase in pressure within the chamber, thawing the biological material inside the chamber, lowering the pressure inside the chamber to the atmospheric pressure and recovering the thawed biological material.

The increase in pressure can be achieved up to a pressure above 20 bars, 30 bars, 40 bars, 50 bars, 60 bars, 70 bars, 80 bars, 90 bars, or 100 bars. Preferably, the pressure is set between 10 and 1000 bars, 10 and 500 bars, 10 and 250 bars, 10 and 100 bars. For example, the pressure may be 10, 20, 30, 40, 50, 60, 70, 80, 90, 100, 150, 200, 250, 300, 350, 400, 450, 500, 725, 1000 bars. Preferably, the pressure is set at the same value as that used in the freezing of the biological material according to the process.

Thawing can be achieved without heat. That is to say, after having brought the chamber to the product shelf temperature and introducing biological material therein, the chamber is not cooled nor heated. Thus, thawing takes place by moving at thermal equilibrium between the chamber and the environment thereof.

Thawing can be carried out by supplying heat, i.e. by heating at a temperature 10° C. above the product melting temperature. Alternatively, thawing can be carried out at a temperature gradient above 1° C./min until the product temperature is below its melting temperature by more than 5° C. (e.g. 2° C./min, 3° C./min, 4° C./min, 5° C./min, 6° C./min, 7° C./min, 8° C./min, 9° C./min, 10° C./min or more), then less than 1° C./min until thawing is completed (e.g. 0.9° C./min, 0.8° C./min, 0.7° C./min, 0.6° C./min, 0.5° C./min, 0.4° C./min, 0.3° C./min, 0.2° C./min, 0° C./min or less). For example, for a product stored at −20° C. and the melting temperature of which is −2° C., thawing may take place with a gradient of 5° C./min from −20° C. to −7° C. and then with a gradient of 0.5° C./minute from −7° C. to 8° C.

EXAMPLES

Example 1: High Pressure Preservation Under Liquid Condition 80 mL of sterilized whole milk (UHT) is inoculated with 400,000 cfu/mL of *Lactobacillus bulgaricus* to form a liquid mixture having a viscosity of 4 cP.

A 2 L container suitable for the process is then filled with liquid dinitrogen before being closed and pressurized so as to achieve the following conditions:
P=75 bars;
T=80 K;
D=800 kg/m3 dinitrogen.

The liquid nitrogen is then present in the chamber in liquid form only, although it is beyond the supercritical pressure.

The liquid mixture is then injected through the top of the container, through a cylindrical nozzle, 3 mm in diameter and 10 mm long, using a piston pump, so that it flows fast dropwise at a rate of about 8 ml/min. Once the 80 mL of the liquid mixture are injected, the pressure is returned to the atmospheric pressure and the container is opened so as to recover a cryogenically frozen product in the form of round beads, which are divided into four 20 mL sterile containers, which are rapidly placed in a freezer at −20° C. The temperature of the solidified organic material generally ranges from −100° C. to −80° C. when the containers are placed in the freezer.

The four containers are respectively brought to room temperature after 24 hours, 48 hours, 1 week (168 hours) and 2 weeks (336 hrs) and two counts of bacteria are made using the TEMPO® LAB method (automated and standardized solution marketed by bioMérieux, based on the most probable number method and adapted to the lactic acid bacteria). For the four samples, the counts are not significantly different and the average population count 5 is 10,000 cfu/mL.

The observed survival rate is thus approximately 93.75%

Example 2: Low Pressure Preservation Under Liquid Condition

Sample preparation is identical to that of Example 1 above.

A suitable 2 L container is then filled with liquid dinitrogen and pressurized so as to obtain the following conditions:
P=20 bars;
T=80K;
D=800 kg/m3 dinitrogen.

The liquid nitrogen is then present in the chamber in liquid form only.

The rest of the procedure is identical to Example 1. The cryogenically frozen product is recovered in the form of round beads.

The four containers are respectively brought to room temperature after 24 hours, 48 hours, 1 week (168 hours) and 2 weeks (336 hrs) and two counts of bacteria are made using the TEMPO® LAB method. For the four samples, the counts are not significantly different and the mean enumerated population is approximately 190,000 cfu/mL The observed survival rate is 47.5%.

Example 3: High Pressure Preservation Under Supercritical Condition

Sample preparation is identical to that of Example 1 above.

A suitable 2 L container is then filled with liquid dinitrogen and pressurized so as to obtain the following conditions:
P=90 bars;
T=150 K;
D=400 kg/m3 dinitrogen.

The liquid nitrogen is then present in the chamber under supercritical form only.

The rest of the procedure is identical to Example 1. The cryogenically frozen product is recovered in the form of round beads.

The four containers are respectively brought to room temperature after 24 hours, 48 hours, 1 week (168 hours) and 2 weeks (336 hrs) and two counts of bacteria are made using the TEMPO® LAB method. For the four samples, the counts are not significantly different and the mean enumerated population is approximately 380,000 cfu/mL.

The observed survival rate is 95%.

Comparative Example 1: Classic Freezing at −20° C.

750 mL of sterilized whole milk (UHT) is inoculated with 400,000 cfu/mL *Lactobacillus bulgaricus* to form a liquid mixture.

20 mL of the liquid mixture are poured into four sterile containers. The containers each containing 20 mL of the liquid mixture are then placed in a freezer at −20° C.

The four containers are respectively brought to room temperature after 24 hours, 48 hours, 1 week (168 hours) and 2 weeks (336 hrs) and two counts of bacteria are made using the TEMPO® LAB method. For the four samples, the counts are negative, i.e. the revivable residual population is less than 1,000 cfu/mL.

The observed survival rate is thus, for the four freezing times at −20° C., less than 0.25%

Comparative Example 2 Under Low Pressure Steam Conditions Preservation

Sample preparation is identical to that of Example 1 above.

A suitable 2 L container is then filled with liquid dinitrogen and pressurized so as to obtain the following conditions:
P=20 bars;
T=80K;
D=80 kg/m3 dinitrogen.

The rest of the procedure is identical to Example 1. The cryogenically frozen product is recovered in the form of a block of frozen product. The block is broken using a spatula so as to distribute the product into the four containers.

The four containers are respectively brought to room temperature after 24 hours, 48 hours, 1 week (168 hours) and 2 weeks (336 hrs) and two counts of bacteria are made using the TEMPO® LAB method. For the four samples, the counts are not significantly different and the average population count 5 is 10,000 cfu/mL.

The observed survival rate is thus approximately 2.5%

Example 4: High Pressure *Spirulina* Preservation 40 g of fresh *Spirulina* (*Arthrospira platensis*), in the form of paste obtained after draining, are added to 40 mL of a water solution containing 5 g/L of sodium chloride resulting in 80 mL of a preparation.

A suitable 2 L container is then filled with liquid dinitrogen and pressurized so as to obtain the following conditions:
P=60 bars;
T=140K;
D=800 kg/m3 dinitrogen.

The nitrogen is then present in the chamber in liquid form.

The preparation is then injected through the top of the container using a piston pump, such that it flows fast dropwise. Once 80 mL of preparation are injected, the pressure is returned to the atmospheric pressure and the reservoir is open so as to recover the cryogenically frozen product, which is distributed into four sterile 20 mL containers, which are quickly placed in a freezer at −20° C. The product temperature generally ranges from −100° C. to −80° C. when the containers are placed in the freezer.

Figure 4:
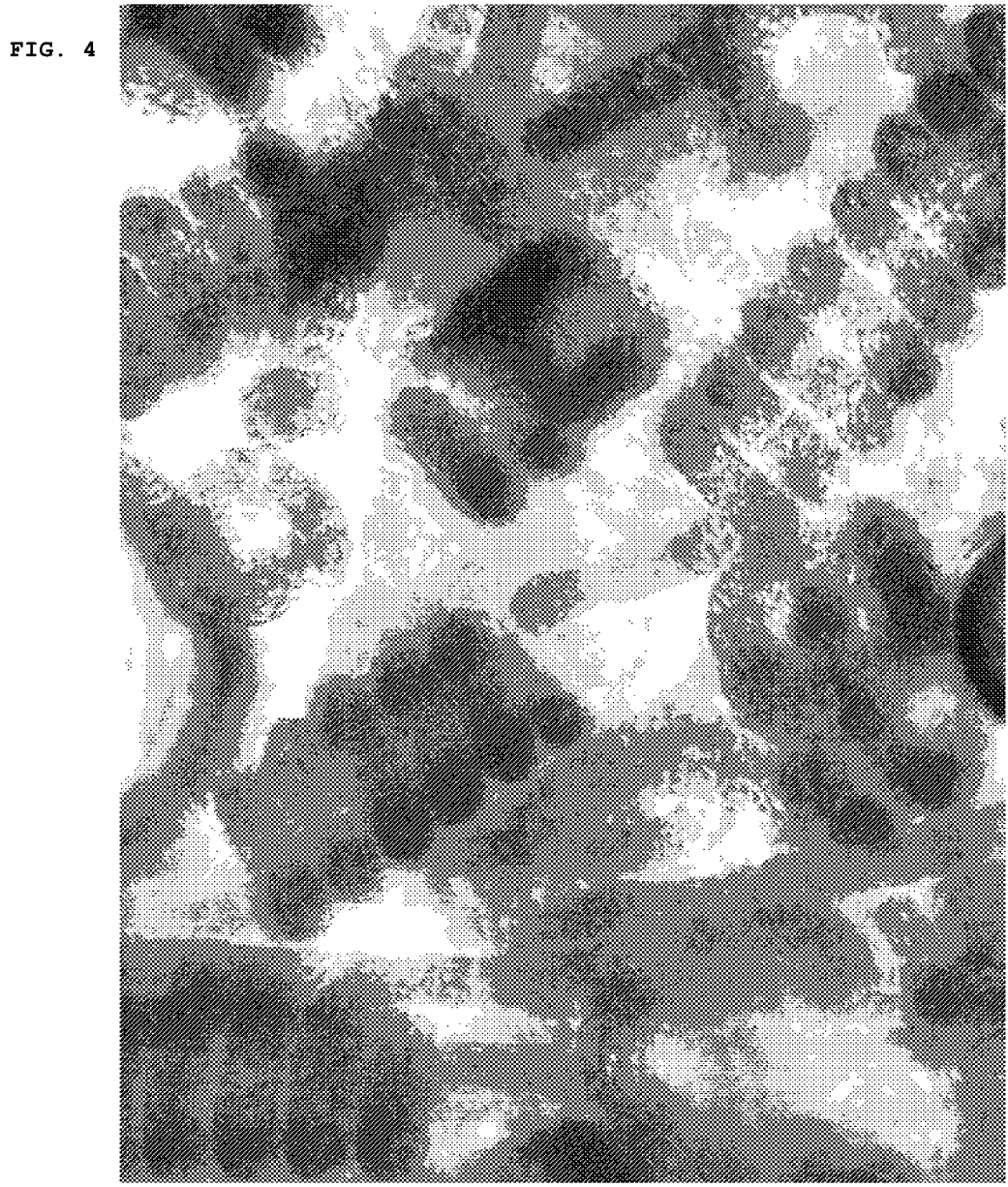
FIG. 4 shows a photography of *spirulina* preserved according to Example 4 and withdrawn after 2 weeks in a freezer at −20° C.

A sample is taken from each of the four containers after 24 hr, respectively, 48 hours, 1 week (168 hours) and 2 weeks (336 hrs). The samples 20 are brought to room temperature and observed under a microscope. No particular alteration was observed in the four samples. FIG. 4 shows a photograph of the last observation.

The invention claimed is:

1. A high pressure cryogenic process for cooling a biological material, comprising a solidification of the biological material by a cryogenic fluid, introducing the biological material into a chamber containing the cryogenic fluid; and
setting desired conditions of temperature, pressure and mass concentration quantity of cryogenic fluid within the chamber to a cryogenic temperature, so that the pressure inside the chamber is at least 10 bar and the mass concentration quantity of cryogenic fluid in the chamber is greater than 200 kg/m3, wherein the solidification of the biological material is carried out at a cryogenic temperature lower than 170 K, wherein the cryogenic fluid is nitrogen in liquid or in supercritical form.

2. The process according to claim 1, wherein the pressure ranges from 10 to 1,000 bars.

3. The process according to claim 2, wherein the pressure ranges from 10 to 500 bars.

4. The process according to claim 3, wherein the pressure ranges from 10 to 100 bars.

5. The process according to claim 1, wherein the pressure is set to be greater than 20 bars.

6. The process according to claim 5, wherein the quantity of cryogenic fluid contained in the chamber is adjusted so as to be greater than 250 kg/m3.

7. The process according to claim 6, wherein the biological material is first contained in suspension in a liquid mixture; setting the cryogenic temperature, the pressure inside the chamber and the quantity of cryogenic fluid is performed prior to the introduction of the biological material into the chamber; and wherein the introduction of the biological material is performed by injection of the liquid mixture into the chamber.

8. The process according to claim 6, wherein the chamber comprises a first chamber portion having an internal volume and a second chamber portion having an internal volume, the internal volumes of the first chamber portion and the second chamber portion to be brought in fluid communication for the solidification of the biological material;
the step of introduction comprising placing the biological material in the first chamber portion free of cryogenic fluid, placing the cryogenic fluid in the second chamber portion and the connection of the first chamber portion with the second chamber portion to form the chamber so that the internal volumes thereof are in fluid communication; and
setting desired conditions of temperature, pressure and quantity of cryogenic fluid being provided in the second chamber portion so as to achieve the desired conditions of temperature, pressure and quantity of cryogenic fluid within the chamber after connecting the first chamber portion with the second chamber portion.

9. A process for the high pressure preservation of a biological material, comprising the steps of the process according to claim 1, further comprising a depressurization of the chamber to an atmospheric pressure and placing the solidified biological material in a freezer.

* * * * *